United States Patent [19]

Byrd, III et al.

[11] Patent Number: 5,466,237

[45] Date of Patent: Nov. 14, 1995

[54] VARIABLE LOCKING STABILIZER ANCHOR SEAT AND SCREW

[75] Inventors: J. Abbott Byrd, III, Virginia Beach, Va.; Rolando M. Puno, Prospect, Ky.; Philip Mellinger, Worthington, Ohio

[73] Assignee: Cross Medical Products, Inc., Columbus, Ohio

[21] Appl. No.: 155,431

[22] Filed: Nov. 19, 1993

[51] Int. Cl.⁶ ............................ A61B 17/70; A61B 17/86
[52] U.S. Cl. .................................................. 606/61; 606/73
[58] Field of Search ........................... 606/61, 53, 54, 606/59, 60, 73

[56] References Cited

U.S. PATENT DOCUMENTS

| | | |
|---|---|---|
| 483,342 | 9/1892 | Bolte . |
| 900,717 | 10/1908 | Feaster . |
| 3,019,504 | 2/1962 | Castagliuolo . |
| 4,011,602 | 3/1977 | Rybicki et al. . |
| 4,289,124 | 9/1981 | Zickel . |
| 4,411,259 | 10/1983 | Drummond . |
| 4,611,581 | 9/1986 | Steffee . |
| 4,641,636 | 2/1987 | Cotrel . |
| 4,648,388 | 3/1987 | Steffee . |
| 4,653,481 | 3/1987 | Howland et al. . |
| 4,655,199 | 4/1987 | Steffee . |
| 4,658,809 | 4/1987 | Ulrich et al. . |
| 4,696,290 | 9/1987 | Steffee . |
| 4,719,905 | 1/1988 | Steffee . |
| 4,771,767 | 9/1988 | Steffee . |
| 4,805,602 | 2/1989 | Puno et al. . |
| 4,815,453 | 3/1989 | Cotrel . |
| 4,887,595 | 12/1989 | Heinig et al. . |
| 4,913,134 | 4/1990 | Luque . |
| 4,950,269 | 8/1990 | Gaines, Jr. . |
| 5,005,562 | 4/1991 | Cotrel . |
| 5,024,213 | 6/1991 | Asher et al. . |
| 5,067,955 | 11/1991 | Cotrel . |
| 5,084,049 | 1/1992 | Asher et al. . |
| 5,113,685 | 5/1992 | Asher et al. . |
| 5,120,171 | 6/1992 | Lasner . |
| 5,129,900 | 7/1992 | Asher et al. . |
| 5,176,678 | 1/1993 | Tsou .......................... 606/61 |
| 5,190,543 | 3/1993 | Schläpfer . |
| 5,207,678 | 5/1993 | Harms et al. . |
| 5,261,913 | 11/1993 | Marnay . |

FOREIGN PATENT DOCUMENTS

| | | |
|---|---|---|
| 0128058 | 12/1984 | European Pat. Off. . |
| 4107480 | 9/1992 | Germany .................. 606/61 |
| 167228 | 7/1921 | United Kingdom . |
| 2173104 | 10/1986 | United Kingdom . |
| 87/07134 | 12/1987 | WIPO . |

*Primary Examiner*—Tamara L. Graysay
*Attorney, Agent, or Firm*—Hudak & Shunk Co.

[57] ABSTRACT

A bone interface anchor is provided for use with a stabilizer rod for the internal fixation of a spine. The anchor has a seat which accommodates the stabilizer rod and which receives a bone screw for the fixation of the seat to the bone. A compression member cooperates with the seat external to the stabilizer rod and can be tightened to cause a compressive force on the stabilizer rod. The stabilizer rod bears on a rounded surface of the bone screw so as to cause a mating interface between the seat and the bone screw. Subsequently, the position of the seat relative to the bone screw can be locked.

16 Claims, 5 Drawing Sheets

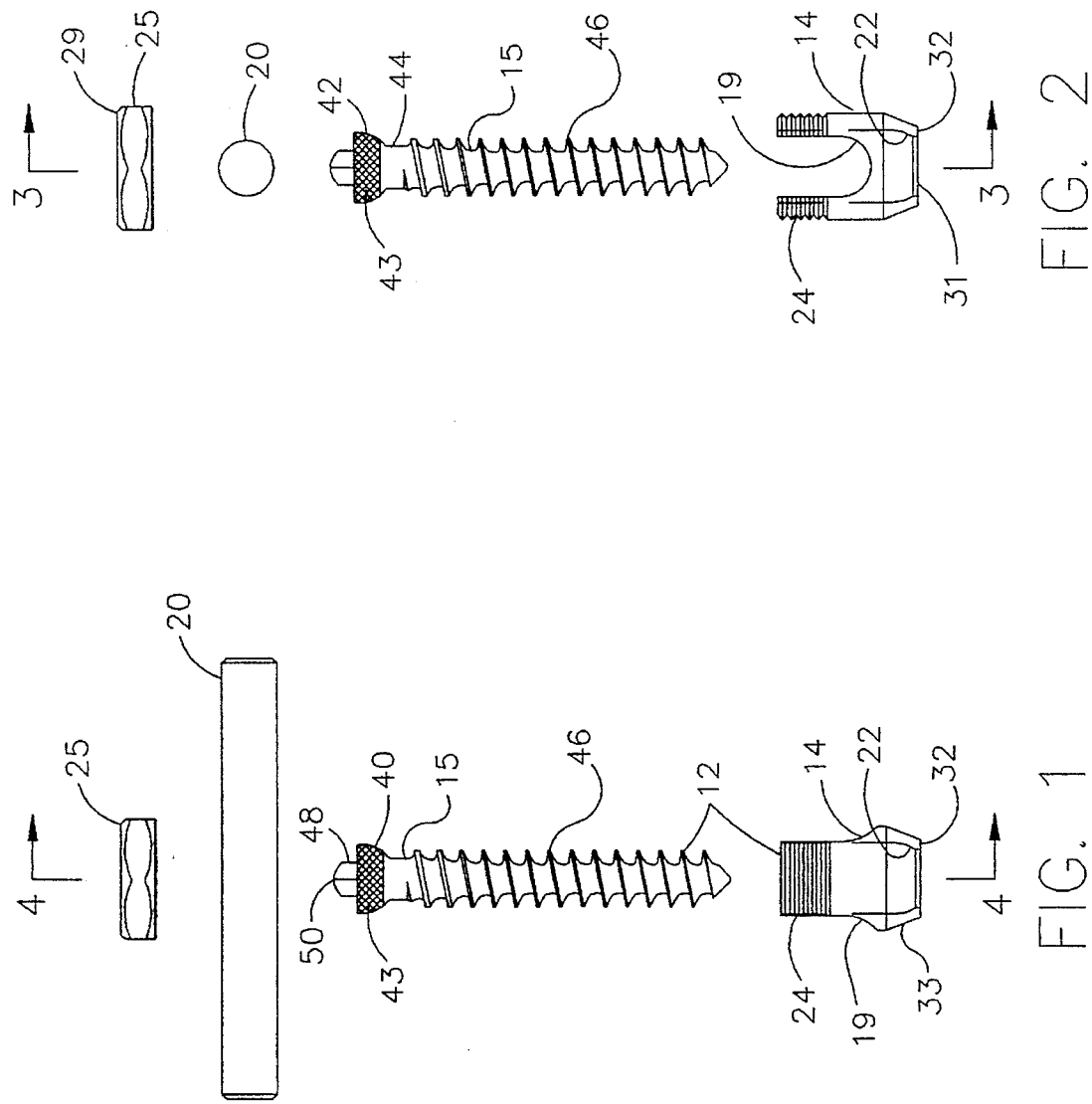

VARIABLE LOCKING STABILIZER ANCHOR SEAT AND SCREW

FIELD OF INVENTION

This invention relates to orthopedic implants, and more particularly to a bone interface anchor for holding a stabilization rod. The anchor can be adjusted after implantation to receive a stabilizer, and is locked into position after assembly.

BACKGROUND

As surgical techniques have advanced, it has become increasingly common for surgeons to use specially designed hardware for the internal fixation of bones. A particular area of concentration for the recent development of this technology has been the spine. Internal fixation is used most frequently in the spine in conjunction with vertebral fusion, and also for the manipulation of the spine to correct spinal deformities such as scoliosis.

There are several important criteria for a hardware system which is used internally for spinal fixation:

1. The implant should provide rigidity as is indicated, generally along the long axis of the patient's spine.

2. The system should be able to accommodate a broad variation in the size and shape of the spinal member with which it is used. For example, the surgeon may wish to use the implant on a variety of individuals. In addition, the difference in the area and size of the point of fixation is compounded by the change in the shape of the vertebrae over the length of the full spinal column. Since it is an advantage to allow the surgeon to master implanting a particular type of assembly, it is preferable if the same or similar anchoring means can be used for a variety of locations. This advantage results in cost efficiency of inventory as well as efficiencies with respect to minimizing the operating time.

3. The hardware must be able to apply and oppose considerable stresses and strains. Thus, the anchor means must be securely fixed to the bone, and the stabilizer must be securely fixed with regard to the anchor means. Moreover, it is desirable to provide the hardware with the integrity to resist breaking.

4. The system should be designed for ease of implantation and removal. Implant hardware is relatively small and therefore somewhat difficult to manipulate. Any difficulty with assembly is compounded by the fact that the assembly occurs during surgery and in a living being. Therefore, it is critical that the hardware is designed with the surgeon's convenience in mind, i.e., to limit the time required and the stress required to implant an assembly. Consequently, a fixation system should be designed to the extent possible for easy assembly while maintaining the option of removal where necessary.

SUMMARY OF THE INVENTION

This invention relates to a variable position locking anchor. The anchor is an assembly comprising the bone fixation means and the stabilizer seat and holding means. More specifically, the anchor assembly comprises a bone screw having a modified ball shaped head and an anchor having a modified socket to receive the screw head. The seat includes a channel which receives the elongated stabilizer means, preferably a rod. The bone screw and the seat socket have a mating configuration which allows adjustment of the position of the seat relative to the bone screw, but which locks the position of the seat relative to the bone screw by means of the application of a compressive force in the direction of the longitudinal axis of the bone screw, which force is applied by the stabilizer means. Thus, the holding means applies a downward compressive force on the stabilizer rod to bias the screw head into an engagement with the screw socket. A preferred method of achieving the locking engagement is to provide knurling on the bottom side of the bone screw, and on the inside surface of the seat screw socket.

It is also advantageous to provide a rounded, high-friction surface on the top of the screw which mates with the rod after assembly. The rounded surface provides for uniform compressive loading by the rod on the screw, and the high-friction surface improves the compressive loading and inhibits slippage along the longitudinal axis of the rod (in contrast a flat surface or a linear surface would tend to cause a biased loading of the screw by the rod since the rod is loaded by the holding means in more than one point).

Thus, it is an object of the present invention to provide a spinal implant assembly which allows for top loading of the stabilizer and top tightening of the assembly, in particular, with respect to the longitudinal stabilizer. It is a further aspect of the invention to provide a stabilizer anchor which is movable with respect to the bone fixation means (i.e., screw) during assembly of the implantation system, but which can be easily locked into position when desired. It is an advantage of the present invention to provide a rod seat which is pivotable with respect to the longitudinal axis of the bone screw as it will accommodate variations in the sites of location, and further, will avoid stressing of the system during manipulation of the spine until the surgeon wishes to lock the system. Specifically, the anchor means including the seat and screw can be implanted, the rod can be inserted into the anchor seat, and the holding means can be loosely applied to the seat in order to avoid the rod disengaging the seat. The seat will be free to move to a limited extent with respect to the screw if the surgeon wants to leave the seat free during manipulation of the spine. Subsequently, the holding means can be tightened down onto the seat to cause a compressive interaction of the rod and bone screw which will lock the bone screw into position relative to the seat.

It is a further object of the present invention to provide a simple anchor assembly comprising limited elements which reduces inventory and makes the implant assembly simpler. More specifically, it is an advantage that the anchor assembly is limited to a bone screw, a seat member, and a compression member. The seat means or the screw can be replaced with various size elements to accommodate variations in patients while minimizing inventory and preserving surgical efficiency.

Moreover, it is an advantage of the present invention to provide a screw surface which is rounded to provide an even loading compressive force from the rod in the direction of the longitudinal axis of the screw and which there avoids biasing of the rod as well as the introduction of stress points along the rod.

BRIEF DESCRIPTION OF DRAWINGS

FIG. 1 is an exploded side plan view of the spinal implant assembly in accordance with the invention;

FIG. 2 is an exploded front view of the spinal implant as shown in FIG. 1;

Figure 3:
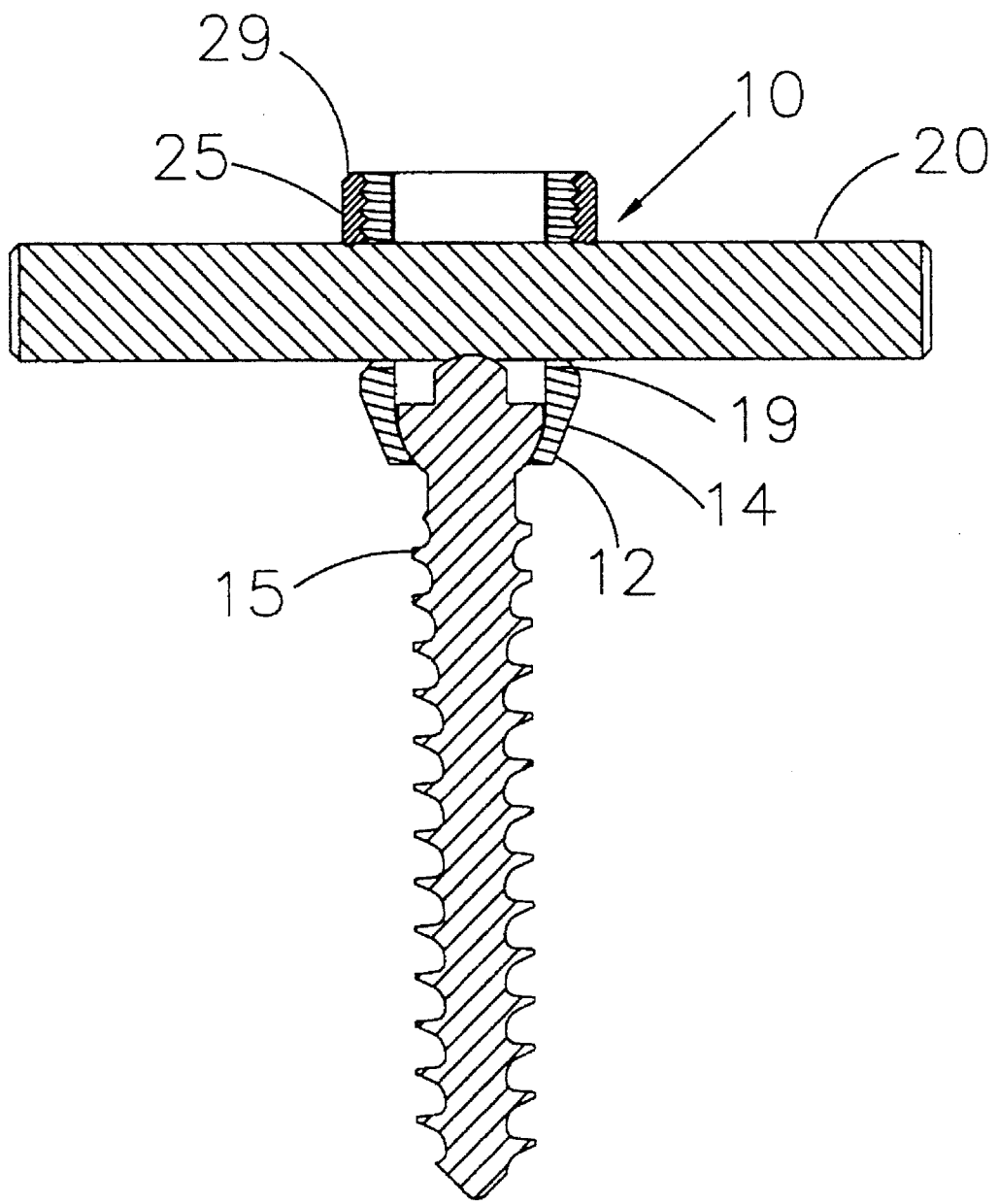
FIG. 3 is a cross-section of the assembly taken along line
Figure 4:
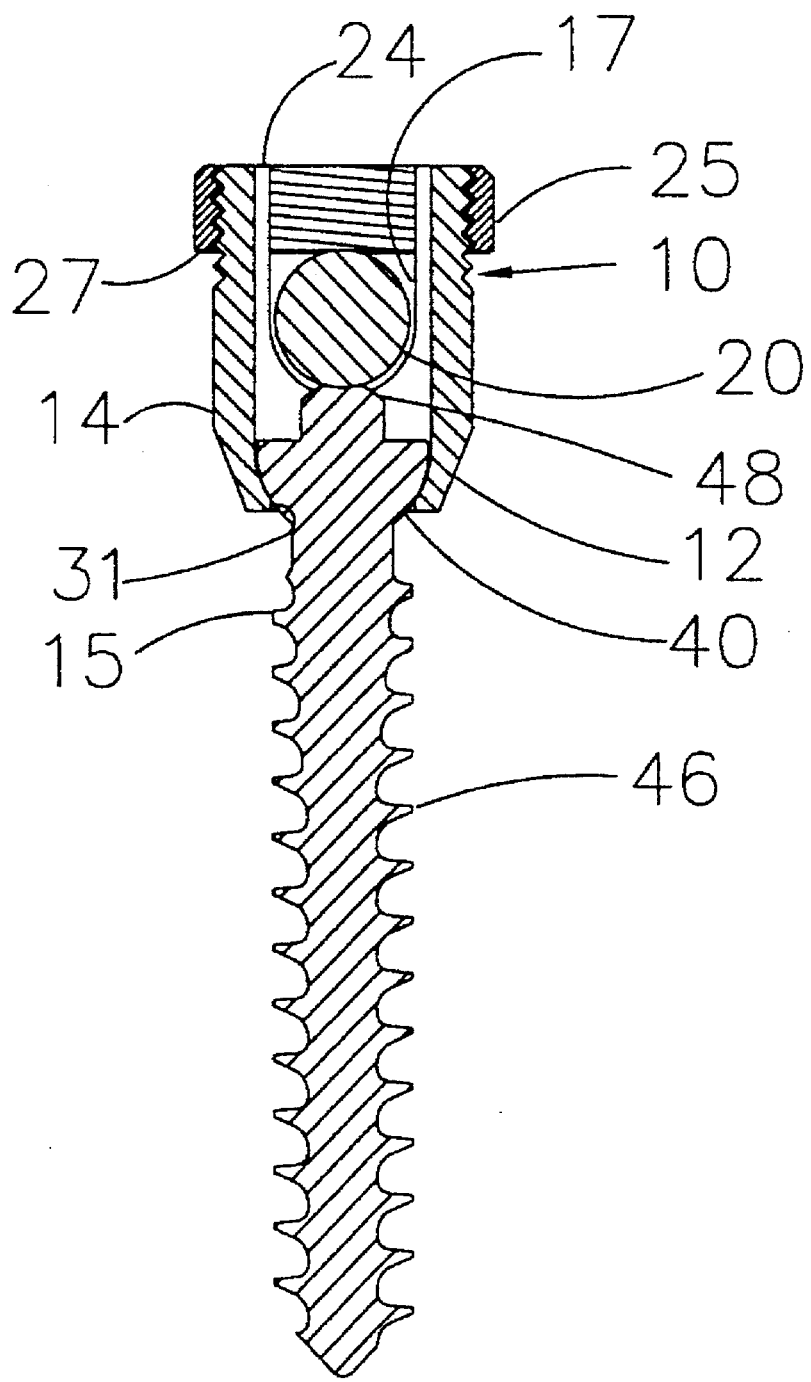
Figure 5:
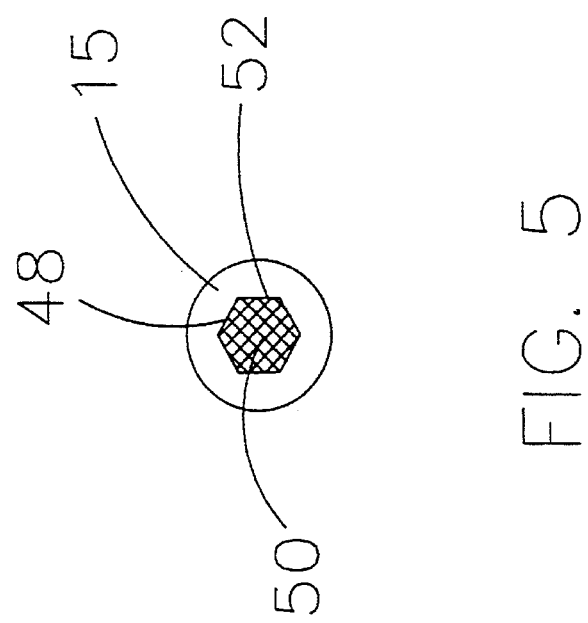
Figure 6:
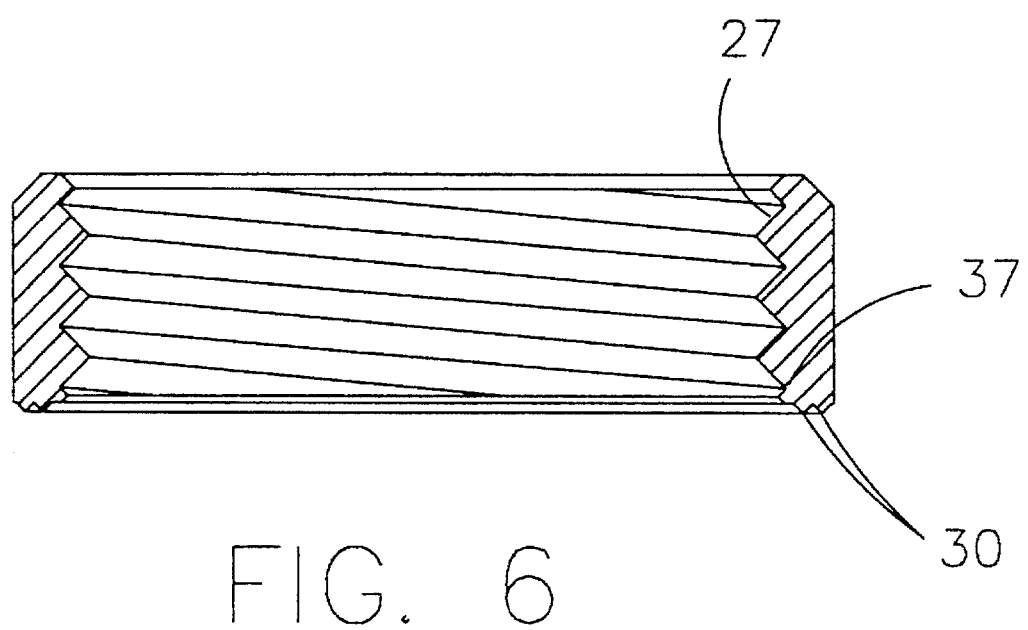

3—3 shown in FIG. 2;

FIG. 4 is a cross-section of the assembly taken in the direction of line 4—4 from FIG. 1;

FIG. 5 is a top plan view of the screw;

FIG. 6 is a cross-section of the nut, and

Figure 7:
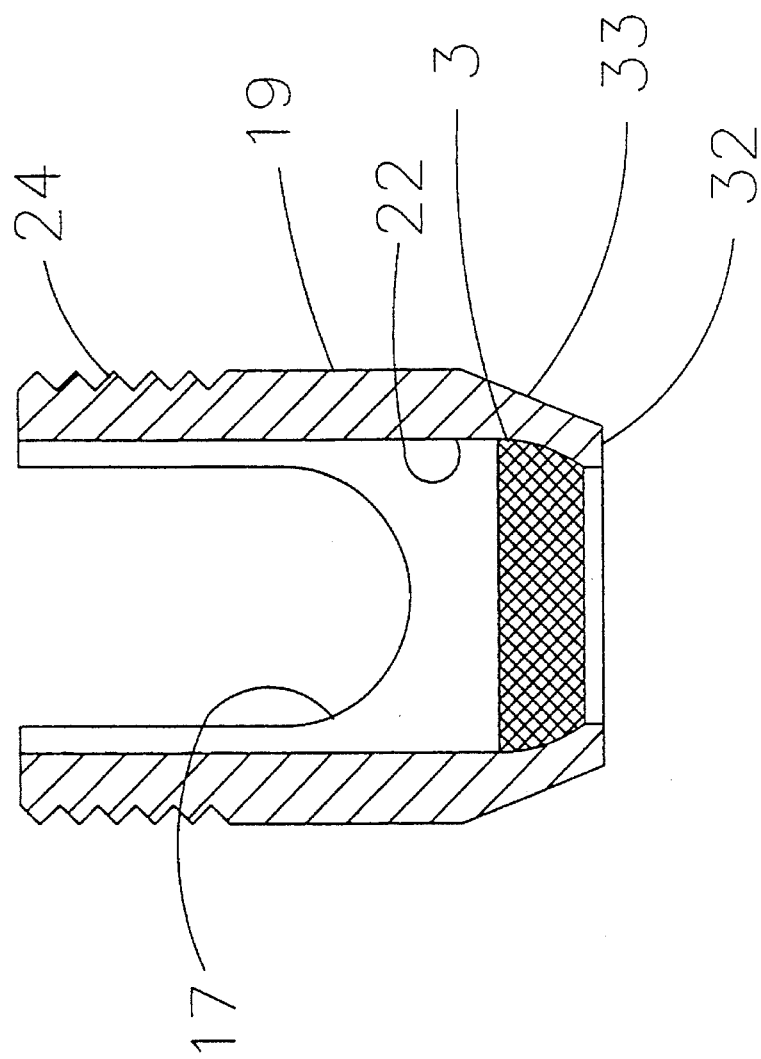

FIG. 7 is an enlarged cross-section of the anchor seat shown in FIG. 4.

DETAILED DESCRIPTION OF THE DRAWINGS

The present invention provides a two-piece assembly which can be assembled and implanted and will allow freedom of movement of the seat 14 relative to the screw and the bone until the compression means, i.e., the nut, is tightened to cause the seat to be locked into position relative to the screw 15.

The present invention relates to a an implant assembly 10 which is used for the fixation and manipulation of the spine. The assembly comprises anchor means 12 which include a seat member 14 and screw or other fixation means 15. While the invention is illustrated primarily with regard to a bone screw, it is envisioned that other bone fixation means could be used instead.

The implant assembly 10 further includes a stabilization means, specifically a rod 20, and holding or compression means, specifically, nut 25.

The anchor seat 14 has an internal bore which forms which forms a socket 22 for the screw 15. The seat 14 further includes a channel 17 which extends in a direction perpendicular to the longitudinal axis of the screw through the seat member. The seat includes a buttressed rod support section 19 on either side of the bore which provides for further stability of the rod along its longitudinal axis.

The seat has a reduced diameter bone interface 32 on its bottom surface and a tapered section 33 below the buttress contour 19. This configuration allows for sufficient material thickness to maintain the integrity of the seat, yet accommodate the bone seat interface.

The implant assembly further includes a nut 25 having internal nut threads 27 which mate with external threads 24 on the seat 14 in order to apply a compressive force on the rod 20. The nut 25 includes a counter bore 37 to facilitate threading the nut on the seat 14. Further, the nut includes a chamfer or rounded edge 29 to reduce the sharp edges of the nut which would be exterior relative to the bone.

In addition, as is shown in FIG. 6, the nut may include a contoured bottom surface 30 to protect the mating interface between the nut and seat threads 24, 27 as well as to improve the compression interface between the nut 25 and rod 20.

More specifically, the screw 15 includes a threaded portion 46 and a screw head 40 which has a modified ball joint 42 on its bottom surface the screw head 40 is separated from the threaded portion 46 by area 44. The ball joint is received in the socket 22 of the seat 14 the area 44 extends through the opening 49 in the seat 14.

Further, as can been seen in FIGS. 1 and 2, the ball section on the bottom of the screw head has a contoured high friction 43, and preferably knurled surface. This knurled surface provides a mating interface with the high friction (i.e., knurled) surface 3 on the interior portion of the socket 22. Further, the top of the screw head includes a projecting external hex 48 having a rounded exterior surface. The external hex can be used to drive the screw into the bone. The rounded surface 50 gives a rounded interface with the rod which provides an even loading of the compressive forces from the rod on the screw. Further, this surface 50 includes a knurl 52.

The variable locking seat and anchor of the present invention presents an advantage to the surgeon in facilitating implantation. More specifically, the surgery is conducted by first exposing the appropriate spinal area, preparing the area for the implantation, and by drilling or probing the bone for initial provision of the screw holes. The surgeon then assembles a seat and screw means by inserting the screw longitudinally through the seat and using a hex driver to screw the screw into the prepared bore while holding the seat in a unitary position relative to the screw. Several anchor assemblies 12 are implanted and a rod can be contoured as is indicated. Since the seat members are still mobile with respect to the screws, the seats may be moved to best accommodate a rod which is aligned between several anchors. After the rod is fit into the rod receiving channel 17 of the anchors 12, nuts 25 may be introduced on the seats 14 to keep retain the rod 20 in the anchor members 12. When the surgeon is ready to lock the position of the seat 14 relative to the bone screw 15, the nut 25 is tightened onto the seat 14. As the nut is biased downward on the seat member, it compresses the rod 20 along the longitudinal axis of the screw 15. The compression is translated from the rod to the rod interface surface 50 which biases the contact of the knurled portion of the screw head 40 into the knurled portion of the ball socket 22. This interface between the screw head 40 and the socket 22 causes a mating contact between the seat and screw such as to lock the relative positions of these components.

Thus, the present invention provides the advantage of a variable position locking seat and screw assembly which is elegantly provided by a minimum of components. Further, the invention has a rod screw interface which applies a uniform compressive force to the rod.

While in accordance with the Patent Statutes, the best mode and preferred embodiment has been set forth, the scope of the invention is not limited thereto, but rather by the scope of the attached claims.

What is claimed is:

1. A bone interface anchor for use with an elongated stabilization member said anchor comprising;

a seat means having retaining means for retaining said stabilization member and compression means for compressively securing said stabilization member within said retaining means, and bone fixation means which secure said anchor member relative to said bone interface, said seat means having a means to form a mating cooperation with said fixation means such that said seat means can be variably positioned relative to said fixation means, and said seat means and said fixation means having means to form a locking interface whereby said stabilization member may be selectively compressively loaded into a cooperation with said fixation means by said compression means so as to lock the relative position between said seat means and said fixation means.

2. An anchor as set forth in claim 1, wherein said retaining means comprise means for retaining a rod.

3. An anchor as set forth in claim 2, wherein said retaining means is a rod channel which is adapted to receive said rod along its longitudinal axis.

4. An anchor as set forth in claim 3, wherein said compression means comprises a compression member which is adapted to bear upon said rod to compress said rod into an engagement with said fixation means.

5. An anchor as set forth in claim 4, wherein said fixation means is a screw having a convexly rounded head, and said seat means includes a concavely rounded socket which receives said screw so as to form a ball and socket joint.

6. An anchor member as set forth in claim 5, wherein said screw head includes a contoured first high-friction surface and said socket member includes a contoured second high-friction surface, whereby said high-friction surfaces are adapted to be biased into a mating engagement by said rod.

7. An anchor as set forth in claim 6, wherein said first and second contoured high friction surfaces are machined.

8. An anchor as set forth in claim 7, wherein said first and second contoured high friction surfaces are knurled.

9. An anchor as set forth in claim 3, wherein said fixation means is a screw having a head and a threaded bone screw distal to said head, wherein said head includes a convexly rounded rod interface surface, and said compression means is adapted to compress said rod into contact with said rod interface surface by a compressive loading in a direction from the head of said screw to the threaded bone screw.

10. An anchor as set forth in claim 9, wherein said compression means is a nut.

11. An anchor as set forth in claim 10, wherein said rod channel has rod supporting contours, said channel including external threads, and said nut including internal threads, said compressive force is adapted to be applied to said rod by said nut by the engagement of said internal and external threads.

12. An anchor for use with a spinal stabilization rod comprising a seat member, a bone screw, and a compressive member, said seat member including an opening about a first axis, said opening forming a socket which receives said screw, said screw having a head including a first convexly rounded surface, which mates with the socket and said head including a second convexly rounded surface for mating with said rod, said seat member further including a opening which forms a channel having an axis in a second direction substantially perpendicular to said first direction, said channel for receiving said rod; and said compressive member applying a compressive force in the direction of the first axis for causing a mating interface between said rod and said rounded surface.

13. An anchor as set forth in claim 12, wherein said mating interface is a high friction interface.

14. An anchor as set forth in claim 13, wherein said first rounded surface mates with said socket to form a ball and socket joint.

15. An anchor as set forth in claim 14, wherein said socket includes a surface which mates with said first convexly rounded surface of said screw head, and at least one of said socket surface and said first convexly rounded surface of said screw head is a high friction surface.

16. An anchor as set forth in claim 15, wherein said high friction surface is a knurled surface.

* * * * *